United States Patent [19]

Eicken et al.

[11] Patent Number: 5,100,458
[45] Date of Patent: Mar. 31, 1992

[54] SALICYCLIC ACID DERIVATIVES AND THEIR USE AS HERBICIDES AND BIOREGULATORS

[75] Inventors: Karl Eicken, Wachenheim; Joachim Rheinheimer; Uwe J. Vogelbacher, both of Ludwigshafen; Karl-Otto Westphalen, Speyer; Bruno Wuerzer, Otterstadt; Wilhelm Rademacher; Klaus Grossmann, both of Limburgerhof, all of Fed. Rep. of Germany

[73] Assignee: BASF Aktinegesellschaft, Ludwigshafen, Fed. Rep. of Germany

[21] Appl. No.: 625,010

[22] Filed: Dec. 10, 1990

[30] Foreign Application Priority Data

Dec. 22, 1989 [DE] Fed. Rep. of Germany ....... 3942476

[51] Int. Cl.$^5$ .................. C07D 239/34; C07D 239/46; A01N 43/54
[52] U.S. Cl. ........................ 71/92; 544/300; 544/301; 544/302; 544/310; 544/312; 544/313; 544/314; 544/316; 544/318
[58] Field of Search ................. 71/92; 544/300, 301, 544/302, 310, 312, 313, 314, 316, 318

[56] References Cited

U.S. PATENT DOCUMENTS

| 4,770,691 | 9/1988 | Nezu et al. | 71/92 |
| 4,889,552 | 12/1989 | Wada et al. | 71/92 |
| 4,900,352 | 2/1990 | Wada et al. | 71/92 |
| 4,946,495 | 8/1990 | Wada et al. | 71/92 |

FOREIGN PATENT DOCUMENTS 0287072 10/1988 European Pat. Off.

*Primary Examiner*—John M. Ford
*Attorney, Agent, or Firm*—Keil & Weinkauf

[57] ABSTRACT

Salicylic acid derivatives of the formula I

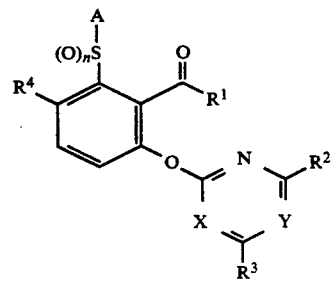

where A is unsubstituted or substituted phenyl, an unsubstituted or substituted five-membered heteroaromatic structure having from two to four nitrogen atoms or having two nitrogen atoms and in addition a sulfur or oxygen atom, or unsubstituted or substituted naphthyl, n is 0, 1 or 2, X and Y are each nitrogen or a methine group and $R^1$ to $R^4$ have the meanings stated in the description, processes and intermediates for their preparation, and their use as herbicides and bioregulators.

5 Claims, No Drawings

SALICYCLIC ACID DERIVATIVES AND THEIR USE AS HERBICIDES AND BIOREGULATORS

The present invention relates to salicylic acid derivatives of the formula I

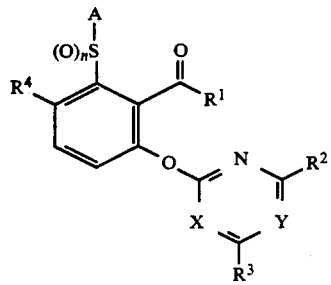

where
- $R^1$ is succinyliminooxy;
  - a 5-membered heteroaromatic structure which contains from one to three nitrogen atoms and may carry from one to four halogen atoms and/or one or two of the following radicals: $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio;
  - a radical —$OR^5$, where $R^5$ is hydrogen, an alkali metal cation, one equivalent of an alkaline earth metal cation or an organic ammonium ion;
  - $C_3$-$C_{12}$-cycloalkyl which may carry from one to three $C_1$-$C_4$-alkyl radicals;
  - $C_1$-$C_{10}$-alkyl which may carry from one to five halogen atoms and/or one of the following radicals: $C_1$-$C_4$-alkoxy, $C_1$-$C_4$-alkylthio, cyano, $C_1$-$C_8$-alkylcarbonyl, $C_1$-$C_8$-alkoxycarbonyl, $C_3$-$C_{12}$-cycloalkyl, phenyl, phenoxy or phenylcarbonyl, where the aromatic radicals may in turn carry from one to five halogen atoms and/or from one to three of the following radicals: $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio; $C_1$-$C_{10}$-alkyl which may carry from one to five halogen atoms and carries one of the following radicals: a 5-membered heteroaromatic structure which contains from one to three nitrogen atoms and may carry from one to four halogen atoms and/or one or two of the following radicals: $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio; $C_2$-$C_6$-alkyl which carries one of the following radicals in the 2-position: $C_1$-$C_6$-alkoximino, $C_3$-$C_6$-alkenyloximino, $C_3$-$C_6$-haloalkenyloximino or benzyloximino;
  - $C_3$-$C_6$-alkenyl or $C_3$-$C_6$-alkynyl, where these groups in turn may carry from one to five halogen atoms, or phenyl which is unsubstituted or monosubstituted to trisubstituted by $C_1$-$C_4$-alkyl or $C_1$-$C_4$-alkoxy or monosubstituted to pentasubstituted by halogen;
- or $R^1$ is a radical $ON{=}CR^6R^7$, where $R^6$ and $R^7$ are each $C_1$-$C_{20}$-alkyl which may carry phenyl, $C_1$-$C_4$-alkoxy and/or $C_1$-$C_4$-alkylthio, or are each phenyl or together form a $C_3$-$C_{12}$-alkylene chain which may carry from one to three $C_1$-$C_3$-alkyl groups;
- $R^2$ and $R^3$ are each $C_1$-$C_4$-alkyl, halogen, $C_1$-$C_4$-haloalkyl, $C_1$-$C_4$-alkoxy, $C_1$-$C_4$-haloalkoxy and/or $C_1$-$C_4$-alkylthio;
- n is zero, 1 or 2;
- X and Y are each a nitrogen atom or a methine group =CH—;
- $R^4$ is hydrogen or $C_1$-$C_4$-alkyl;
- A is an unsubstituted or monosubstituted to trisubstituted or, where halogen is the substituent, monosubstituted to pentasubstituted phenyl radical

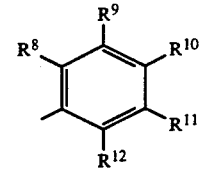

where $R^8$–$R^{12}$ are each hydrogen, halogen, cyano or nitro;
$C_3$-$C_6$-alkenyl, $C_3$-$C_6$-alkenyloxy, $C_3$-$C_6$-alkynyloxy or $C_3$-$C_6$-alkynyl, where these groups in turn may carry from one to five halogen atoms;
di-$C_1$-$C_4$-alkylamino, $C_3$-$C_8$-cycloalkyl which may carry from one to three $C_1$-$C_4$-alkyl radicals;
$C_1$-$C_{10}$-alkoxycarbonyl, $C_1$-$C_4$-alkylthio; phenoxy, where the aromatic radical may carry from one to five halogen atoms and/or from one to three of the following radicals: $C_1$-$C_4$-alkyl, $C_1$-$C_4$-haloalkyl, $C_1$-$C_4$-haloalkoxy, $C_1$-$C_4$-alkoxy and $C_1$-$C_4$-alkylthio, or a $C_1$-$C_{10}$-alkyl or alkoxy group which may carry from one to five halogen atoms and/or one of the following radicals: $C_1$-$C_4$-alkoxy, $C_1$-$C_4$-alkylthio, phenyl or phenoxy, where the aromatic radicals in turn may carry from one to five halogen atoms and/or from one to three of the following radicals: $C_1$-$C_4$-alkyl, $C_1$-$C_4$-haloalkyl, $C_1$-$C_4$-haloalkoxy and $C_1$-$C_4$-alkylthio;
or A is naphthyl which may carry from one to three halogen atoms and/or from one to three of the following radicals: $C_1$-$C_4$-alkyl or $C_1$- or $C_2$-haloalkyl, and environmentally compatible salts of the compounds I.

The present invention furthermore relates to processes for the preparation of the compounds I and their use as herbicides and growth regulators, and novel salicylic acid derivatives of the formula II'

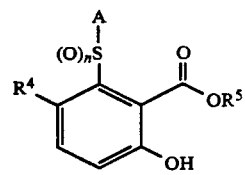

as intermediates for the preparation of the compounds I.
In the formula II',
- $R^5$ is hydrogen, an alkali metal cation, one equivalent of an alkaline earth metal cation on an organic ammonium ion;
- $C_1$-$C_{10}$-alkyl which may carry from one to five halogen atoms and/or one of the following radicals: $C_1$-$C_4$-alkoxy, $C_1$-$C_4$-alkylthio, phenyl and phenoxy, where each of the phenyl radicals may carry from one to five halogen atoms and/or from one to three of the following radicals: $C_1$-$C_4$-alkyl, $C_1$–$C_4$-haloalkyl, $C_1$–$C_4$-alkoxy, $C_1$–$C_4$-haloalkoxy and/or $C_1$–$C_4$-alkylthio; n is zero, 1 or 2;

$R^4$ is hydrogen or $C_1$–$C_4$-alkyl, and

A is a monosubstituted to trisubstituted or, where halogen is the substituent, monosubstituted to pentasubstituted phenyl radical

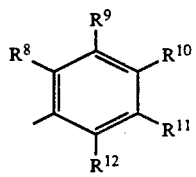

where $R^8$–$R^{12}$ are each hydrogen, halogen, cyano or nitro;

$C_3$–$C_6$-alkenyl, $C_3$–$C_6$-alkenyloxy, $C_3$–$C_6$-alkynyloxy or $C_3$–$C_6$-alkynyl, where these groups in turn may carry from one to five halogen atoms;

di-$C_1$–$C_4$-alkylamino, $C_3$–$C_8$-cycloalkyl which may carry from one to three $C_1$–$C_4$-alkyl radicals;

$C_1$–$C_{10}$-alkoxycarbonyl, $C_1$–$C_4$-alkylthio;

phenoxy, where the aromatic radical may carry from one to five halogen atoms and/or from one to three of the following radicals: $C_1$–$C_4$-alkyl, $C_1$–$C_4$-haloalkyl, $C_1$–$C_4$-haloalkoxy, $C_1$–$C_4$-alkoxy and $C_1$–$C_4$-alkylthio; a $C_1$–$C_{10}$-alkyl or alkoxy group which may carry from one to five halogen atoms and/or one of the following radicals: $C_1$–$C_4$-alkoxy, $C_1$–$C_4$-alkylthio, phenyl or phenoxy, where the aromatic radicals in turn may carry from one to five halogen atoms and/or from one to three of the following radicals: $C_1$–$C_4$-alkyl, $C_1$–$C_4$-haloalkyl, $C_1$–$C_4$-haloalkoxy and $C_1$–$C_4$-alkylthio;

or A is naphthyl which may carry from one to three halogen atoms and/or from one to three of the following radicals: $C_1$–$C_4$-alkyl or $C_1$- or $C_2$-haloalkyl.

The literature (EP-A 223 406, EP-A 249 708, EP-A 287 072 and EP-A 287 079) describes herbicidal substituted salicylic acids. However, their action is unsatisfactory.

It is an object of the present invention to provide novel salicylic acid derivatives having improved herbicidal properties and possessing plant growth-regulating properties.

We have found that this object is achieved by the compounds of the formula I which are defined at the outset. We have furthermore found processes for the preparation of the compounds I and methods for controlling undesirable plant growth with the compounds I. We have also found that salicylic acid derivatives of the general formula I defined above have excellent plant growth-regulating properties. The novel salicylic acid derivatives II' have been found, these derivatives being intermediates for the preparation of the compounds I.

The compounds of the formula I are obtained, for example, by reacting a correspondingly substituted salicylic acid derivative of the formula II with an appropriate compound of the formula III in the presence of a base.

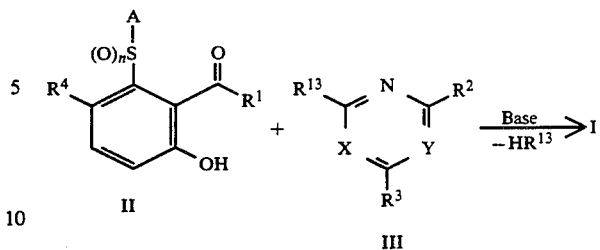

In formula III, $R^{13}$ is a conventional nucleofugic leaving group, for example halogen, such as chorine, bromine or iodine, aryl- or alkylsulfonyl, such as toluenesulfonyl or methylsulfonyl, or another equivalent leaving group. Compounds of the the formula III having a reactive substituent $R^{13}$ are known, for example 2,4,6-trichloropyrimidine, 2-alkylthio- or arylthio-4,6-dichloropyrimidine or cyanuric chloride, or are readily obtainable on the basis of the general technical knowledge. Suitable bases are alkali metal or alkaline earth metal hydrides, such as NaH and $CaH_2$, alkali metal hydroxides, such as NaOH and KOH, alkali metal alcoholates, such as potassium tert-butylate, alkali metal carbonates, such as $Na_2CO_3$ and $K_2CO_3$, alkali metal amides, such as $NaNH_2$ and lithium diisopropylamide, or tertiary amines. When an inorganic base is used, a phase transfer catalyst may be added if it enhances the conversion.

Where the compounds of the formula I prepared in the manner described are carboxylic acids (i.e. where $R^1$ is hydroxyl), other compounds described can also be prepared therefrom, for example by first converting the carboxylic acid in a conventional manner into an activated form, such as a halide or imidazolide, and then reacting this with the corresponding hydroxy compound. These two steps can also be simplified, for example, by allowing the carboxylic acid to act on the hydroxy compound in the presence of a water-eliminating agent, such as a carbodiimide.

Where n is zero and $R^1$ is a lower alkoxy radical, the intermediates of the formula II can be prepared, in accordance with the scheme below, from a 2-chloromalonate of the formula IV and unsubstituted or substituted thiophenol HS-A in the presence of an inorganic or organic base, the product then being subjected to a thermal cyclization reaction at from 100° to 350° C.

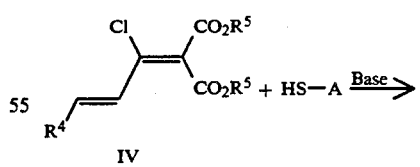

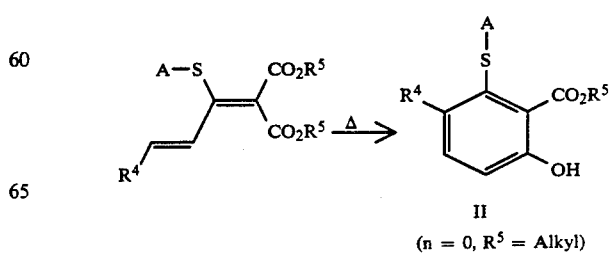

(n = 0, $R^5$ = Alkyl)

The 2-chloromalonate IV used as a starting material is readily obtainable, for example by reacting a corresponding acyl malonate with a chlorinating agent, such as phosphorus oxychloride, in the presence of tributylamine, as described in J. Org. Chem. 53 (1988), 881.

The intermediates of the formula II (n=0) prepared as described above are usually obtained as alkyl esters. These can be hydrolyzed by known processes to give the carboxylic acids. The latter can then be converted by methods known from the literature into various esters which are required for the preparation of active ingredients of the formula I as claimed in claim 1. The novel intermediates of the formula II' are obtained in a similar manner.

For the preparation of the active ingredients of the formula I where n is 1 or 2, as claimed in claim 1, the active ingredients of the formula I where n is zero can be reacted with suitable oxidizing agents to give the sulfoxide or sulfone derivative. Alternatively, the intermediates of the formula II (n=0) can also be oxidized with suitable oxidizing agents. Suitable oxidizing agents are per acids, e.g. m-chloroperbenzoic acid or peracetic acid, and hydrogen peroxide.

With regard to the herbicidal activity, preferred compounds I are those in which the substituents have the following meanings:

$R^1$ is succinyliminooxy;

5-membered hetaryl, such as pyrrolyl, pyrazolyl, imidazolyl or triazolyl, in particular imidazolyl or pyrazolyl, where the aromatic radical is bonded via nitrogen and in turn may carry from one to four halogen atoms as stated above, in particular fluorine or chlorine, and/or one or two of the following radicals:

alkyl, such as methyl, ethyl, propyl, 1-methylethyl, butyl, 1-methylpropyl, 2-methylpropyl and 1,1-dimethylethyl, preferably methyl, ethyl and 1-methylethyl; haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluroethyl, 2,2,2-trichloroethyl and pentafluoroethyl, in partiuclar difluoromethyl, trifluoromethyl, 2,2,2-trifluoroethyl and pentafluoroethyl;

alkoxy as stated above, having from one to four carbon atoms;

haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluroethoxy, 2,2,2-trifluoroethoxy, 2-chloro-1,1,2-trifluoroethoxy and pentafluoroethoxy, in particular trifluoromethoxy, and/or alkylthio, such as methylthio, ethylthio, propylthio, 1-methylethylthio, butylthio, 1-methylpropylthio, 2-methylpropylthio and 1,1-dimethylethylthio, in particular methylthio and ethylthio;

or $R^1$ is a radical $OR^5$, where $R^5$ is hydrogen, the cation of an alkali metal or the cation of an alkaline earth metal, such as lithium, sodium, potassium, calcium, magnesium and barium, or an environmentally compatible organic ammonium ion;

alkyl, in particular methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethyl-butyl, 2-ethylbutyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 1-propylbutyl and octyl, which may carry from one to five of the abovementioned halogen atoms, in particular fluorine and chlorine, and/or one of the following radicals: cyano, alkoxy or alkylthio of from one to four carbon atoms, as stated above, in particular methoxy, ethoxy, 1-methylethoxy and methylthio; alkylcarbonyl, in particular methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl and 1-ethyl-2-methylpropyl carbonyl;

alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylethoxycarbonyl, n-pentyloxycarbonyl, 1-methylbutoxycarbonyl, 2-methylbutoxycarbonyl, 3-methylbutoxycarbonyl, 1,2-methylpropoxycarbonyl, 1,1-dimethylpropoxycarbonyl, 2,2-dimethylpropoxycarbonyl, 1-ethylpropoxycarbonyl, n-hexyloxycarbonyl, 1-methylpentyloxycarbonyl, 2-methylpentyloxycarbonyl, 3-methylpentyloxycarbonyl, 4-methylpentyloxycarbonyl, 1,2-dimethylbutoxycarbonyl, 1,3-dimethylbutoxycarbonyl, 2,3-dimethylbutoxycarbonyl, 1,1-dimethylbutoxycarbonyl, 2,2-dimethylbutoxycarbonyl, 3,3-dimethylbutoxycarbonyl, 1,1,2-trimethylpropoxycarbonyl, 1,2,2-trimethylpropoxycarbonyl, 1-ethylbutoxycarbonyl, 2-ethylbutoxycarbonyl, 1-ethyl-2-methylpropoxycarbonyl, n-heptyloxycarbonyl, 1-methylhexyloxycarbonyl, 2-methylhexyloxycarbonyl, 3-methylhexyloxycarbonyl, 4-methylhexyloxycarbonyl, 5-methylhexyloxycarbonyl, 1-ethylpentyloxycarbonyl, 2-ethylpentyloxycarbonyl, 1-propylbutoxycarbonyl and octyloxycarbonyl, in particular methoxycarbonyl, ethoxycarbonyl, 1-methylethoxycarbonyl and 1-methylpropoxycarbonyl;

phenyl, phenoxy or phenylcarbonyl, where these aromatic radicals may in turn carry from one to five halogen atoms as stated above, in particular fluorine or chlorine and bromine, and/or from one to three of the following radicals:

alkyl, haloalkyl, alkoxy, haloalkoxy and/or alkylthio, each of from one to four carbon atoms, as stated in general and in particular above, or $C_1-C_{10}$-alkyl as stated above, which may carry from one to five halogen atoms, such as fluorine, chlorine, bromine or iodine, in particular fluorine or chlorine, and may additionally carries one of the following radicals: 5-membered hetaryl having from one to three nitrogen atoms, as stated above for $R^1$;

$C_2$–$C_6$-alkyl, in particular $C_2$–$C_4$-alkyl, which is substituted in the 2-position by $C_1$–$C_6$-alkoximino, e.g. methoximino, ethoximino or propoximino; $C_3$–$C_6$-alkenyloximino, such as 2-propenyloximino, 2-butenyloximino or 3-butenyloximino; $C_3$–$C_6$-haloalkenyloximino, such as 3,3-dichloro-2-propenyloximino, 2,3,3-trichloro-2-propenyloximino or benzyloximino;

alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl-, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl and 3-methyl-2-pentenyl;

alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably 2-propynyl, 2-butynyl, 1-methyl-2-propynyl and 1-methyl-2-butynyl, in particular 2-propynyl, where these alkenyl and alkynyl groups may carry from one to five of the halogen atoms stated above in general and in particular;

$C_3$–$C_{12}$-cycloalkyl, in particular $C_3$–$C_6$-cycloalkyl, such as cyclopropyl, cyclobutyl, cyclopentyl or cyclohexyl, which is unsubstituted or substituted by from one to three $C_1$–$C_4$-alkyl radicals;

phenyl which is unsubstituted or monosubstituted to trisubstituted by $C_1$–$C_4$-alkyl or -alkoxy, such as methyl, ethyl, propyl, butyl, methoxy or ethoxy or phenyl which is substituted by from one to five halogen atoms, e.g. chlorine or fluorine;

or $R^1$ is a radical $ON=CR^6R^7$, where $R^6$ and $R^7$ are each straight-chain or branched $C_1$–$C_{20}$-alkyl, preferably $C_1$–$C_{15}$-alkyl, in particular $C_1$–$C_9$-alkyl, which may carry a phenyl, a $C_1$–$C_4$-alkoxy or a $C_1$–$C_4$-alkylthio radical, or are each phenyl or together form $C_3$–$C_{12}$-alkylene, preferably $C_4$–$C_7$-alkylene, which may carry from one to three $C_1$–$C_3$-alkyl groups, preferably methyl or ethyl;

$R^2$ and $R^3$ are in general and in particular the alkyl groups, halogen atoms, haloalkyl groups, alkoxy groups, haloalkoxy groups and/or alkylthio groups stated for $R^1$, each of from 1 to 4 carbon atoms;

X and Y are each nitrogen or a methine group $=CH-$; $R^4$ is hydrogen or alkyl of from one to four, in particular one to three, carbon atoms, for example methyl, ethyl, n-propyl or isopropyl;

A is unsubstituted or substituted phenyl where suitable substituents $R^8$ to $R^{12}$ are: halogen, such as fluorine, chlorine, bromine or iodine; cyano, nitro; unsubstituted or halogen-substituted alkenyl, alkenyloxy, alkynyloxy or alkynyl, each of from 3 to 6 carbon atoms; di-$C_1$–$C_4$-alkylamino, such as dimethylamino, diethylamino, dipropylamino, di-1-methylethylamino, dibutylamino, di-1-methylpropylamino, di-2-methylpropylamino, di-1,1-dimethylethylamino, ethylmethylamino, propylmethylamino, 1-methylethylmethylamino or butylmethylamino; unsubstituted or alkyl-substituted cycloalkyl as stated above for $R^5$, alkoxycarbonyl or alkylthio as stated above for $R^5$, unsubstituted or substituted phenoxy as stated under $R^5$, $C_1$–$C_{10}$-alkyl or alkoxy, in particular $C_1$–$C_6$-alkyl or alkoxy, preferably $C_1$–$C_4$-alkyl or alkoxy, which are unsubstituted or substituted by the stated radicals, examples of substituted phenyl radicals A being the following:

2-fluorophenyl, 3-fluorophenyl, 4-fluorophenyl, 2,6-difluorophenyl, 2,4-difluorophenyl, 2-fluoro-4-trifluoromethylphenyl, 2,3-difluorophenyl, 2-chlorophenyl, 3-chlorophenyl, 2-iodophenyl, 2-bromophenyl, 2-chloro-6-fluorophenyl, pentafluorophenyl, pentachlorophenyl, 2,4-dichlorophenyl, 2,6-dichlorophenyl, 2-chloro-4-fluorophenyl, 3,5-dichlorophenyl, 2-chloro-6-methylphenyl, 2,3,5-trichlorophenyl, 2-methylphenyl, 3-methylphenyl, 4-methylphenyl, 2,6-dimethylphenyl, 2,4-dimethylphenyl, 3,5-dimethylphenyl, 2,4,6-trimethylphenyl, 2-chloro-4-methylphenyl, 2-methoxyphenyl, 4-methoxyphenyl, 4-chloro-2-methoxyphenyl, 2-trifluoromethylphenyl, 2,3-dimethyl-4-methoxyphenyl, 4-dimethylamino-2-methylphenyl, 3-cyanophenyl, 3-nitrophenyl, 3-phenoxyphenyl, 3-(3-trifluoromethylphenoxy)-phenyl and 3-trifluoromethylphenyl.

Naphthyl radicals A which may be substituted are, for example 1-naphthyl and 2-naphthyl.

Particularly preferred compounds of the formula I are those in which $R^2$ and $R^3$ are each methoxy, methyl, difluoromethoxy or chlorine, $R^4$ is hydrogen or methyl, X is nitrogen, Y is a methine group and $R^1$ and A have the meanings stated in the claims.

Suitable salts of the compounds of the formula I are environmentally compatible salts, for example alkali metal salts, in particular the potassium or sodium salt, alkaline earth metal salts, in particular the calcium, magnesium or barium salt, manganese salts, copper salts, zinc salts or iron salts and ammonium, phosphonium, sulfonium or sulfoxonium salts, for example ammonium salts, tetraalkylammonium salts, benzyltrialkylammonium salts, trialkylsulfonium salts or trialkylsulfoxonium salts.

EXAMPLE 1

2-(4,6-Dimethoxypyrimidin-2-yloxy)-6-phenylthiobenzoic acid (compound No. 1.002)

a) Ethyl 3-phenylthio-2-ethoxycarbonyl-2,4-hexadienecarboxylate 12 g (0.12 mol) of triethylamine are added dropwise to a solution of 25.0 g (0.1 mol) of 3-chloro-2-ethoxycarbonyl-2,4-hexadienecarboxylate and 13.5 g (0.12 mol) of thiophenol in 75 ml of chloroform under nitrogen (exclusion of oxygen), and the mixture is then stirred under reflux for 12 hours. After washing, drying and evaporation of the solvent, the above compound is obtained as a crude product (27.5 g of an oil).

b) Ethyl 6-phenylthiosalicylate 27.5 g of the above oil are heated in a distillation apparatus at a bath temperature of 240°-250° C., while stirring, until elimination of ethanol (5 ml of distillate) has ended. The cooled residue is dissolved in 10% strength NaOH and the solution is extracted once with ether. After acidification of the aqueous phase with concentrated HCl, extraction of the product with ether, drying and evaporation of the solvent, 15 g (55%) of the above ester (bp. 200° C./10, mp. 48°-50° C.) are isolated.

c) 6-Phenylthiosalicylic acid 0.85 g (3.1 mmol) of ethyl 6-phenylthiosalicylates are refluxed for one hour in a solution of 0.45 g (6.8 mmol) of 85% strength potassium hydroxide in 5 ml of water. After cooling, the reaction mixture is acidified to pH 3 with orthophosphoric acid. After the crystals have been filtered off under suction and dried, 0.7 g (91%) of the product of melting point 150° C. (decomposition) is obtained.

d) 2-(4,6-Dimethoxypyrimidin-2-yloxy)-6-phenylthiobenzoic aicd 0.55 g (4.9 mmol) of potassium tert-butylate is added a little at a time to a solution of 0.6 g (2.4 mmol) of 6-phenylthiosalicylic acid in 8 ml of dimethyl sulfoxide, the temperature increasing to 35° C. The mixture is cooled to room temperature, after which 0.53 g (2.4 mmol) of 4,6-dimethoxy-2-methylsulfonylpyrimidine is added and stirring is carried out for one hour at room temperature. The content of the flask is poured onto a mixture of 100 ml of cold water, 1 ml of orthophosphoric acid and 50 ml of ether. The ether phase is washed with 5% strength phosphoric acid and water, dried and evaporated down. After the crude product has been stirred with cold toluene, 0.50 g (54%) of the above product of melting point 135°-136° C. is isolated.

EXAMPLE 2

General method for the preparation of aromatic carboxylic oxime esters or similar compounds of the formula I 3.2 mmol of the particular aromatic 2-(4,6-dimethoxypyrimidin-2-yloxy)-carboxylic acid are initially taken in 20 ml of dimethoxyethane and 3.2 mmol of sodium hydride are added, evolution of gas occurring immediately. Stirring is continued for one hour at room temperature, the mixture is cooled to 0° C. and 3.5 mmol of oxalyl chloride are added. Stirring is continued for one hour at 0° C., after which about 30% of the solvent are evaporated under reduced pressure to remove the excess oxalyl chloride. 4.2 mmol of the particular oxime or of a similar hydroxy compound, dissolved in 10 ml of dimethoxyethane, and then 3.2 mmol of pyrimidine are added at 0° C., and the mixture is warmed up to room temperature in the course of one hour. It is poured into 120 ml of cold water and extracted with methylene chloride. The organic phase is dried over sodium sulfate and evaporated down under reduced pressure. The remaining substance can be further purified by chromatography over silica gel.

TABLE 1

Salicylic acid derivatives of the Formula I (where $X = N$ and $R^2 = OCH_3$)

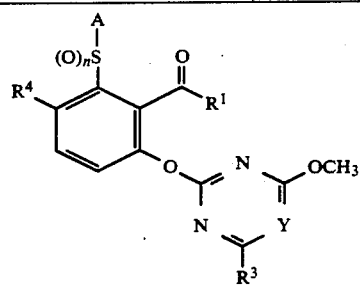

I

| No. | $R^1$ | $R^3$ | $R^4$ | A | n | Y | phys. data m.p. [°C.] |
|---|---|---|---|---|---|---|---|
| 1.001 | OH | $OCH_3$ | H | Phenyl | 0 | N | |
| 1.002 | OH | $OCH_3$ | H | Phenyl | 0 | CH | 135-136 |
| 1.003 | $OCH_3$ | $OCH_3$ | H | Phenyl | 0 | CH | |
| 1.004 | $OC_2H_5$ | $OCH_3$ | H | Phenyl | 0 | CH | |
| 1.005 | 2-Propeniminoxy | $OCH_3$ | H | Phenyl | 0 | CH | |
| 1.006 | Methylthiomethyloxy | $OCH_3$ | H | Phenyl | 0 | CH | |
| 1.007 | Ethoxycarbonylmethyloxy | $OCH_3$ | H | Phenyl | 0 | CH | |
| 1.008 | Propargyloxy | $OCH_3$ | H | Phenyl | 0 | CH | |
| 1.009 | OH | $OCH_3$ | H | 2-Fluorophenyl | 0 | CH | |
| 1.010 | OH | $OCH_3$ | H | 3-Fluorophenyl | 0 | CH | |
| 1.011 | OH | $OCH_3$ | H | 4-Fluorophenyl | 0 | CH | 240 |
| 1.012 | OH | $OCH_3$ | H | 2-Chlorophenyl | 0 | CH | |

TABLE 1-continued

Salicylic acid derivatives of the Formula I (where X = N and $R^2$ = $OCH_3$)

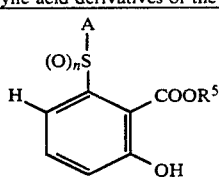

| No. | $R^1$ | $R^3$ | $R^4$ | A | n | Y | phys. data m.p. [°C.] |
|---|---|---|---|---|---|---|---|
| 1.013 | OH | $OCH_3$ | H | 3-Chlorophenyl | 0 | CH | 142–144 |
| 1.014 | OH | $OCH_3$ | H | 4-Chlorophenyl | 0 | CH | 160 |
| 1.015 | OH | $OCH_3$ | H | 2,4-Dichlorophenyl | 0 | CH | |
| 1.016 | OH | $OCH_3$ | H | 2,5-Dichlorophenyl | 0 | CH | |
| 1.017 | OH | $OCH_3$ | H | 2,4,5-Trichlorophenyl | 0 | CH | |
| 1.018 | OH | $OCH_3$ | H | 2,3,4-Trichlorophenyl | 0 | CH | |
| 1.019 | OH | $OCH_3$ | H | 2-Methylphenyl | 0 | CH | |
| 1.020 | OH | $OCH_3$ | H | 3-Methylphenyl | 0 | CH | 152 |
| 1.021 | OH | $OCH_3$ | H | 4-Methylphenyl | 0 | CH | 163–165 |
| 1.022 | OH | $OCH_3$ | H | 2,4-Dimethylphenyl | 0 | CH | |
| 1.023 | OH | $OCH_3$ | H | 2-Isopropylphenyl | 0 | CH | |
| 1.024 | OH | $OCH_3$ | H | 4-tert.Butylphenyl | 0 | CH | |
| 1.025 | OH | $OCH_3$ | H | 2-Methoxyphenyl | 0 | CH | |
| 1.026 | OH | $OCH_3$ | H | 3-Methoxyphenyl | 0 | CH | |
| 1.027 | OH | $OCH_3$ | H | 4-Methoxyphenyl | 0 | CH | |
| 1.028 | OH | $OCH_3$ | H | 4-Phenoxyphenyl | 0 | CH | |
| 1.029 | OH | $OCH_3$ | H | 4-Bromophenyl | 0 | CH | |
| 1.030 | OH | $OCH_3$ | H | 3-Trifluoromethylphenyl | 0 | CH | |
| 1.031 | OH | $OCH_3$ | H | 3-Nitrophenyl | 0 | CH | |
| 1.032 | OH | $OCH_3$ | H | 4-Nitrophenyl | 0 | CH | |
| 1.033 | OH | $OCH_3$ | H | Naphth-1-yl | 0 | CH | |
| 1.034 | OH | $OCH_3$ | H | Naphth-2-yl | 0 | CH | |
| 1.035 | OH | $OCH_3$ | H | Phenyl | 1 | CH | |
| 1.036 | $OC_2H_5$ | $OCH_3$ | H | Phenyl | 1 | CH | |
| 1.037 | OH | $OCH_3$ | H | Phenyl | 2 | CH | 168–170 |
| 1.038 | $OC_2H_5$ | $OCH_3$ | H | Phenyl | 2 | CH | |

TABLE 2

Salicylic acid derivatives of the formula II'

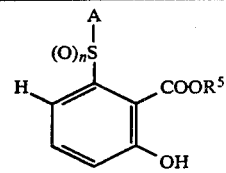

| No. | $R^5$ | A | n | phys. data m.p. [°C.] |
|---|---|---|---|---|
| 2.001 | H | Phenyl | 0 | 150 (decomp.) |
| 2.002 | $C_2H_5$ | Phenyl | 0 | 48–50 |
| 2.003 | H | 2-Fluorophenyl | 0 | |
| 2.004 | H | 3-Fluorophenyl | 0 | |
| 2.005 | H | 4-Fluorophenyl | 0 | |
| 2.006 | H | 2-Chlorophenyl | 0 | |
| 2.007 | H | 3-Chlorophenyl | 0 | |
| 2.008 | H | 4-Chlorophenyl | 0 | |
| 2.009 | H | 2,4-Dichlorophenyl | 0 | |
| 2.010 | H | 2,5-Dichlorophenyl | 0 | |
| 2.011 | H | 2,4,5-Trichlorophenyl | 0 | |
| 2.012 | H | 2,3,4-Trichlorophenyl | 0 | |
| 2.013 | H | 2-Methylphenyl | 0 | |
| 2.014 | H | 3-Methylphenyl | 0 | |
| 2.015 | H | 4-Methylphenyl | 0 | |
| 2.016 | H | 2,4-Dimethylphenyl | 0 | |
| 2.017 | H | 2-Isopropylphenyl | 0 | |
| 2.018 | H | 4-tert.Butylphenyl | 0 | |
| 2.019 | H | 2-Methoxyphenyl | 0 | |
| 2.020 | H | 3-Methoxyphenyl | 0 | |
| 2.021 | H | 4-Methoxyphenyl | 0 | |
| 2.022 | H | 4-Phenoxyphenyl | 0 | |
| 2.023 | H | 4-Bromophenyl | 0 | |
| 2.024 | H | 3-Trifluoromethylphenyl | 0 | |
| 2.025 | H | 3-Nitrophenyl | 0 | |
| 2.026 | H | 4-Nitrophenyl | 0 | |
| 2.027 | H | Naphth-1-yl | 0 | |
| 2.028 | H | Naphth-2-yl | 0 | |
| 2.029 | H | Phenyl | 1 | |
| 2.030 | $C_2H_5$ | Phenyl | 1 | |
| 2.031 | H | Phenyl | 2 | |
| 2.032 | $C_2H_5$ | Phenyl | 2 | |

The novel herbicidal and growth-regulating compounds I and the agents containing them can be used for example in the form of directly sprayable solutions, powders, suspensions, including concentrated aqueous, oily or other suspensions or dispersions, emulsions, oil dispersions, pastes, dusts, broadcasting agents or granules, by spraying, atomizing, dusting, broadcasting or pouring. The application forms depend on the intended uses; they should in any case ensure very fine distribution of the novel active ingredients.

The compounds I are suitable in general for the preparation of directly sprayable solutions, emulsions, pastes or oil dispersions. Suitable inert additives are mineral oil fractions having a medium to high boiling point, such as kerosene or diesel oil, as well as coal tar oils and oils of vegetable or animal origin, aliphatic, cyclic and aromatic hydrocarbons, e.g. toluene, xylene, paraffin, tetrahydronaphthalene, alkylated naphthalenes or their derivatives, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. For the preparation of emulsions, pastes or oil dispersions, the substrates, as such or dissolved in an oil or solvent, can be homogenized in water by means of wetting agents, adhesives, dispersants or emulsifiers. However, concentrates which are suitable for dilution with water and consist of active substance, wetting agent, adhesive, dispersant or emulsifier and, if required solvent or oil can also be prepared.

Suitable surfactants are the alkali metal, alkaline earth metal and ammonium salts of aromatic sulfonic acids, for example lignin-, phenol-, naphthalene- and dibutylnaphthalenesulfonic acid, and of fatty acids, alkyl- and alkylarylsulfonates, alkyl-, laurylether- and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or naphthalenesulfonic acids with phenol and formaldehyde, polyoxyethylene octylphenol ether, ethoxylated isooctyl-, octyl- or nonylphenol, alkylphenol-, tributylphenylpolyglycol ether, alkylaryl polyether alcohols, isotridecyl alcohol, fatty alcohol ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders, broadcasting agents and dusts can be prepared by mixing the active substances with a solid carrier or milling the active substances together with a solid carrier.

Granules, for example coated, impregnated and homogeneous granules, can be prepared by binding the active ingredients to solid carriers. Solid carriers are mineral earths, such as silica gel, silicas, silicates, talc, kaolin, limestone, lime, chalk, bole, loess, clay, dolomite, diatomacerus earth, calcium sulfate, magnesium sulfate, magnesium oxide, milled plastics, fertilizers, such as ammonium sulfate, ammonium phosphate, ammonium nitrate, ureas and vegetable products, such as cereal meal, ground bark, woodmeal and nutshell meal, cellulose powder or other solid carriers.

The formulations contain from 0.1 to 95, preferably from 0.5 to 90, % by weight of active ingredient. The active ingredients are used in a purity of from 90 to 100%, preferably from 95% to 100% (according to NMR spectrum).

The novel compounds I can be formulated, for example, as follows:

I. 90 parts by weight of compound No. 1.002 are mixed with 10 parts by weight of N-methyl-α-pyrrolidone, and a solution suitable for use in the form of very small drops is obtained.

II. 20 parts by weight of compound No. 1.002 are dissolved in a mixture which consists of 80 parts by weight of xylene, 10 parts by weight of the adduct of from 8 to 10 moles of ethylene oxide with 1 mole of oleic acid N-monoethanolamide, 5 parts by weight of the calcium salt of dodecylbenzenesulfonic acid and 5 parts by weight of the adduct of 40 moles of ethylene oxide with 1 mole of castor oil. By pouring the solution into 100,000 parts by weight of water and finely distributing the solution therein, an aqueous dispersion which contains 0.02% by weight of the active ingredient is obtained.

III. 20 parts by weight of compound No. 1.002 are dissolved in a mixture which consists of 40 parts by weight of cyclohexanone, 30 parts by weight of isobutanol, 20 parts by weight of the adduct of 7 moles of ethylene oxide with 1 mole of isooctylphenol and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

IV. 20 parts by weight of active ingredient No. 1.002 are dissolved in a mixture which consists of 25 parts by weight of cyclohexanone, 65 parts by weight of a mineral oil fraction boiling within a range from 210° to 280° C. and 10 parts by weight of the adduct of 40 moles of ethylene oxide with 1 mole of castor oil. By pouring the solution into 100,000 parts by weight of water and finely distributing the solution therein, an aqueous dispersion which contains 0.02% by weight of the active ingredient is obtained.

V. 20 parts by weight of the active ingredient No. 1.002 are thoroughly mixed with 3 parts by weight of the sodium salt of diisobutylnaphthalene-α-sulfonic acid, 17 parts by weight of the sodium salt of a ligninsulfonic acid from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

VI. 3 parts by weight of active ingredient No. 1.002 are mixed with 97 parts by weight of finely divided kaolin. A dust which contains 3% by weight of the active ingredient is obtained in this manner.

VII. 30 parts by weight of active ingredient No. 1.002 are thoroughly mixed with a mixture of 92 parts by weight of a silica gel powder and 8 parts by weight of liquid paraffin which has been sprayed beforehand onto the surface of the silica gel. A preparation of the active ingredient having good adhesion is obtained in this manner.

VIII. 20 parts by weight of active ingredient No. 1.002 are thoroughly mixed with 2 parts by weight of the calcium salt of dodecylbenzenesulfonic acid, 8 parts by weight of fatty alcohol polyglycol ether, 2 parts by weight of the sodium salt of a phenol-/urea/formaldehyde condensate and 68 parts by weight of a paraffinic mineral oil. A stable oily dispersion is obtained.

IX. 90 parts by weight of a compound No. 1.002 are mixed with 10 parts by weight of N-methyl-α-pyrrolidone, and a solution suitable for use in the form of very small drops is obtained.

X. 20 parts by weight of compound No. 1.002 are disolved in a mixture which consists of 80 parts by weight of xylene, 10 parts by weight of the adduct of from 8 to 10 moles of ethylene oxide with 1 mole of oleic acid N-monoethanolamide, 5 parts by weight of the calcium salt of dodecylbenzenesulfonic acid and 5 parts by weight of the adduct of 40 moles of ethylene oxide with 1 mole of castor oil. By pouring the solution into 100,000 parts by weight of water and finely distributing the solution therein, an aqueous dispersion which contains 0.02% by weight of the active ingredient is obtained.

XI. 20 parts by weight of compound No. 1.002 are dissolved in a mixture which consists of 40 parts by weight of cyclohexanone, 30 parts by weight of isobutanol, 20 parts by weight of the adduct of 7 moles of ethylene oxide with 1 mole of isooctylphenol and 10 parts by weight of the adduct of 40 moles of ethylene oxide with 1 mole of castor oil. By pouring the solution into 100,000 parts by weight of water and finely distributing the solution therein, an aqueous dispersion which contains 0.02% by weight of the active ingredient is obtained.

XII. 20 parts by weight of active ingredient No. 1.002 are dissolved in a mixture which consists of 25 parts by weight of cyclohexanol, 65 parts by weight of a mineral oil fraction boiling within a range from 210° to 280° C. and 10 parts by weight of the adduct of 40 moles of ethylene oxide with 1 mole of castor oil. By pouring the solution into 100,000 parts by weight of water and finely distributing the solution therein, an aqueous dispersion which contains 0.02% by weight of the active ingredient is obtained.

XIII. 20 parts by weight of active ingredient No. 1.002 are thoroughly mixed with 3 parts by weight of the sodium salt of diisobutylnaphthalene-α-sulfonic acid, 17 parts by weight of the sodium salt of a ligninsulfonic acid from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

XIV. 3 parts by weight of the active ingredient No. 1.002 are mixed with 97 parts by weight of finely divided kaolin. A dust which contains 3% by weight of active ingredient is obtained in this manner.

XV. 30 parts by weight of active ingredient No. 1.002 are thoroughly mixed with a mixture of 92 parts by weight of silica gel powder and 8 parts by weight of liquid paraffin, which has been sprayed onto the surface of the silica gel. A preparation of the active ingredient having good adhesion is obtained in this manner.

XVI. 20 parts by weight of active ingredient No. 1.002 are thoroughly mixed with 2 parts by weight of the calcium salt of dodecylbenzenesulfonic acid, 8 parts by weight of fatty alcohol polyglycol ether, 2 parts by weight of the sodium salt of a phenolsulfonic acid/formaldehyde condensate and 68 parts by weight of a paraffinic mineral oil. A stable oily dispersion is obtained.

The herbicidal and growth-regulating agents or the active ingredients can be applied by the preemergence or postemergence method. If the active ingredients are less well tolerated by certain crops, it is possible to use application methods in which the herbicidal agents are sprayed with the aid of the sprayers in such a way that the said herbicidical agents as far as possible do not come into contact with the leaves of the sensitive crops while the active ingredients reach the leaves of undesirable plants growing underneath or the uncovered soil surface (post-directed, lay-by).

The application rates of herbicidal active ingredient are from 0.001 to 3.0, preferably from 0.005 to 0.5, kg/ha of active substance (a.s.), depending on the aim of control, the season, the target plants and the stage of growth.

The salicylic acid derivatives of the formula I which have a growth-regulating action can have a different effect on virtually all stages of development of a plant and are therefore used as growth regulators. The wide range of actions of the plant growth regulators depends in particular a) on the plant species and variety,
b) on the time of application, based on the stage of development of the plant and on the season,
c) on the place and method of application (for example seed dressing, soil treatment, application to foliage or trunk injection in the case of trees),
d) on climatic factors, eg. temperature, amount of precipitation and also length of day and light intensity,
e) on the nature of the soil (including fertilizer application),
f) on formulation or application form of the active ingredient, and finally
g) on the concentrations of active substance used.

From the number of different possibilities for the application of the novel plant growth regulators of the formula Ia in plant cultivation in agriculture and in horticulture, a few are stated below.

A. With the compounds which can be used according to the invention, it is possible greatly to inhibit the vegetative growth of the plants, which is expressed in particular in a reduction of the growth in length. Accordingly, the treated plants have inhibited growth; moreover, a darker leaf coloration is observed.

Reduced intensity of growth of grasses on road edges, hedges, canal banks and lawn areas, such as parks, sports grounds, orchards, ornamental lawns and airfields, has proven advantageous in practice, so that labor-intensive and expensive cutting of the grass can be reduced.

The increase in the strength of crops susceptible to lodging, such as cereals, corn, sunflowers and soybean, is also of economic interest. The resulting shortening and strengthening of the stem reduce or eliminate the danger of lodging (bending) of plants in unfavorable weather conditions before the harvest.

The use of growth regulators for inhibiting the growth in length and for changing the course of ripening in cotton is also important. This permits completely mechanized harvesting of this important crop.

In fruit trees and other trees, it is possible to save pruning costs with the growth regulators. Furthermore, the alternation of fruit trees can be interrupted by growth regulators.

By using growth regulators, it is also possible to increase or inhibit the lateral branching of plants. This is of interest if, for example in tobacco plants, it is intended to inhibit the formation of side shoots (suckers), in favor of leaf growth.

Using growth regulators, it is also possible considerably to increase the frost resistance, for example in winter rape. On the one hand, the growth in length and the development of leaf or plant mass which is too luxurious (and therefore particularly susceptible to frost) are inhibited. On the other hand, the young rape plants are retarded in the vegetative development stage after sowing and before the onset of the winter frosts, in spite of advantageous growth conditions. As a result, the danger of frost affecting plants which tend toward premature termination of inhibition of flowering and to a transition to the generative phase is also eliminated. In other crops too, for example winter cereals, it is advantageous if the crops are well tillered in autumn through treatment with novel compounds but do not start winter with growth which is too luxurious. The increased sensitivity to frost and, owing to the relatively low leaf or plant mass, attack by various diseases (for example fungal disease) can therefore be prevented. Furthermore, inhibition of vegetative growth permits denser planting of the soil in the case of many crops, so that a greater yield, based on the soil area, can be achieved.

B. Using the growth regulators, it is possible to achieve greater yields of both parts of plants and plant ingredients. For example, it is possible to induce the growth of greater amounts of buds, blooms, leaves, fruits, seed grains, roots and tubers, to increase the content of sugar in sugar beets, sugar cane and citrus fruits, to increase the protein content of cereals or soybean or to stimulate rubber trees to achieve increased latex flow.

The salicylic acid derivatives of the formula I can increase the yield by intervening in the plant metabolism or by promoting or inhibiting vegetative and/or generative growth.

C. Finally, plant growth regulators can be used both for shortening or prolonging the development stages and for accelerating or delaying ripening of the harvested plant parts before or after harvesting.

For example, facilitating harvesting is of economic interest, this being permitted by concentrated dropping or reduction in the adhesion to the tree at a particular time in the case of citrus fruits, olives or other species and varieties of pomes, stone fruit and shell-fruit. The same mechanism, ie. promotion of the formation of abscission tissue between fruit or leaf part and sprout part of the plant, is also essential for easily controllable defoliation of crops, for example cotton.

D. Furthermore, the water consumption of plants can be reduced using growth regulators. This is particularly important for arable areas which have to be artificially irrigated at high cost, for example in arid or semiarid areas. By using the novel substances, it is possible to reduce the intensity of irrigation and hence carry out more economical farming. Under the influence of growth regulators, the available water is better utilized because, inter alia, the extent of opening of the stomata is reduced,
a thicker epidermis and a thicker cuticle are formed,
root penetration of the soil is improved and
the microclimate in the crop is favorably influenced by more compact growth.

The active ingredients of the formula I which are to be used according to the invention can be fed to the crops both via the seed (as seed dressings) and via the soil, i.e. through the root, and, particularly preferably, by spraying over the foliage.

Because of the good toleration by plants, the application rate can be greatly varied.

In the case of seed treatment, in general amounts of active ingredient of from 0.001 to 50, preferably from 0.01 to 10, g per kilogram of seed are required.

For foliage and soil treatment, in general doses of from 0.001 to 10, preferably from 0.01 to 3, in particular from 0.01 to 0.5, kg/ha are considered sufficient.

The herbicides or the active ingredients can be applied by the preemergence or postemergence method. If the active ingredients are less well tolerated by certain crops, it is possible to use application methods in which the herbicides are sprayed by means of sprayers so that the herbicides as far as possible do not come into contact with the leaves of the sensitive crops while the active ingredients reach the leaves of undesirable plants growing underneath or the uncovered soil (post-directed, lay-by).

The application rates of active ingredient are from 0.001 to 3.0, preferably from 0.01 to 1.0, kg/ha of active substance (a.s.), depending on the aim of control, the season, the target plants and the stage of growth.

In view of the wide range of application methods, the novel compounds or agents containing them can also be used in a number of further crops for eliminating undesirable plants. For example, the following crops are suitable:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugar beets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | beets |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora*, *Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elaeis guineensis* | oil palms |
| *Fragaria vesca* | strawberries |
| *Glycine max* | soybeans |
| *Gossypium hirsutum* (*Gossypium arboreum* *Gossypium herbaceum* *Gossypium vitifolium*) | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |

-continued

| Botanical name | Common name |
| --- | --- |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To broaden the action spectrum and to achieve synergistic effects, the novel compounds I can be mixed with many members of other groups of herbicidal or growth-regulating active ingredients and applied together with the said active ingredients. Examples of suitable components for the mixture are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives, quinolinecarboxylic acid derivatives, aryloxy- and hetaryloxyphenoxypropionic acids and their salts, esters and amides, etc.

Furthermore, it may be useful if the compounds I, alone or in combination with other herbicides, are mixed with further crop protection agents and applied together with these, for example with agents for controlling pests or phytopathogenic fungi or bacteria. The miscibility with mineral salt solutions, which are used for eliminating nutrient and trace element deficiencies, is also of interest. Nonphytotoxic oils and oil concentrates may also be added.

USE EXAMPLES

The herbicidal action of the salicylic acid derivatives I is demonstrated in greenhouse experiments.

The vessels employed were plastic flowerpots having a volume of 300 cm$^3$ and filled with a sandy loam containing about 3.0% humus. The seeds of the test plants were sown separately, according to species.

For the preemergence treatment, the active ingredients, suspended or emulsified in water, were applied to the surface of the soil through finely distributing nozzles immediately after the seeds had been sown. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with the compounds, suspended or emulsified in water. The application rate for post-emergence treatment was 0.125 kg/ha.

The pots were set up in the greenhouse, heat-loving species at 20° to 35° C., and species from moderate climates at 10° to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants used in the greenhouse experiments were Chenopodium album, Amaranthus retroflexus and Sesbania exaltata.

Compound no. 1.002, employed postemergence at a rate of 0.125 kg/ha, provides excellent control of unwanted broadleaved plants.

The growth-regulating action of the salicylic acid derivatives I will be apparent from Examples A and B.

EXAMPLE A

Investigation of the growth-regulating action of compound no. 1.002 in a system with duckweed (Lemna paucicostata)

The plants were grown photomixotrophically (addition of 1% saccharose in an in organic nutrient medium) under sterile conditions in permanent light. The candidate substances were dissolved in acetone and added to the duckweeds in amounts of $10^{-7}$ to $10^{-10}$ mol/liter. After 8 days the increase in fresh weight of the plants was determined and the growth-regulating action of the abovementioned compound was calculated as a percentage growth inhibition of the control (0=no inhibition, 100=total growth inhibition).

| Application rate (mol × $1^{-1}$) | Growth inhibition |
| --- | --- |
| $10^{-7}$ | 95 |
| $10^{-8}$ | 89 |
| $10^{-9}$ | 5 |
| $10^{-10}$ | 0 |

EXAMPLE B

To determine the growth-regulating properties of compound no. 1.002, the test plants were grown in plastic pots approx. 12.5 cm in diameter in a substrate provided with sufficient nutrients.

The candidate compound was sprayed onto the plants postemergence as an aqueous formulation. The growth-regulating action observed was confirmed at the end of the experiment by measuring the height of the plants. The values obtained were compared with the height of the untreated plants.

The reduction in height was also accompanied by a deeper leaf coloration. The increased chlorophyll content is indicative of an increased rate of photosynthesis, making for bigger yields.

The individual data are given in Tables B.1 and B.2.

TABLE B.1

Spring barley, "Aramir" Postemergence treatment

| Compound No. | Concentration mg of a.i./vessel | Relative growth height |
|---|---|---|
| untreated | — | 100 |
| 1.002 | 0.0063 | 103.0 |
|  | 0.0125 | 99.7 |
|  | 0.05 | 88.0 |
|  | 0.1 | 78.1 |
|  | 0.4 | 56.5 |

TABLE B.2

Spring wheat, "Ralle" Postemergence treatment

| Compound No. | Concentration mg of a.i./vessel | Relative growth height |
|---|---|---|
| untreated | — | 100 |
| 1.002 | 0.0063 | 99.0 |
|  | 0.0125 | 95.8 |
|  | 0.05 | 92.7 |
|  | 0.1 | 76.7 |
|  | 0.4 | 54.3 |

We claim:

1. A salicylic acid derivative of the formula I

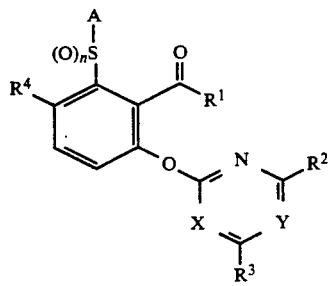

where $R^1$ is succinylimidooxy;

a 5-membered heteroaromatic structure selected from the group consisting of pyrrolyl, pyrazolyl, imidazolyl and triazolyl, where the aromatic radical is bonded via nitrogen and in turn may carry from one to four halogen atoms and/or one or two of the following radicals: methyl, ethyl, propyl, 1-methylethyl, butyl, 1-methylpropyl, 2-methylpropyl and 1,1-dimethylethyl, fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl, alkoxy having from one to four carbon atoms; difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2,-trifluoroethoxy, 2-chloro-1,1,2-trifluoroethoxy and pentafluoroethoxy, and/or methylthio, ethylthio, propylthio, 1-methylethylthio, butylthio, 1-methylpropylthio, 2-methylpropylthio and 1,1-dimethylethylthio;

a radical —$OR^5$, where $R^5$ is hydrogen, an alkali metal cation, one equivalent of an alkaline earth metal cation or an organic ammonium ion;

$C_3$-$C_{12}$-cycloalkyl which may carry from one to three $C_1$-$C_4$-alkyl radicals;

$C_1$-$C_{10}$-alkyl which may carry from one to five halogen atoms and/or one of the following radicals: $C_1$-$C_4$-alkoxy, $C_1$-$C_4$-alkylthio, cyano, $C_1$-$C_8$-alkoxycarbonyl, $C_1$-$C_{12}$-cycloalkyl, phenyl, phenoxy or phenylcarbonyl, where the aromatic radicals may in turn carry from one to five halogen atoms and/or from one to three of the following radicals: $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio;

$C_1$-$C_{10}$-alkyl which may carry from one to five halogen atoms and carries one of the following radicals: a 5-membered heteroaromatic structure; selected from the group consisting of pyrrolyl, pyrazolyl, imidazolyl and triazolyl, where the aromatic radical is bonded via nitrogen and in turn may carry from one to four halogen atoms and/or one or two of the following radicals: methyl, ethyl, propyl, 1-methylethyl, butyl, 1-methylpropyl, 2-methylpropyl and 1,1-dimethylethyl, fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl, alkoxy having from one to four carbon atoms; difluoromethoxy, trifluoromethoxy, chlorodifluoromethoxy, dichlorofluoromethoxy, 1-fluoroethoxy, 2fluoroethoxy, 2,2-difluoroethoxy, 1,1,2,2-tetrafluoroethoxy, 2,2,2,-trifluoroethoxy, 2-chloro-1,1,2-trifluoroethoxy and pentafluoroethoxy, and/or methylthio, ethylthio, propylthio, 1-methylethylthio, butylthio, 1-methylpropylthio, 2-methylpropylthio and 1,1-dimethylethylthio; $C_2$-$C_8$-alkyl which carries one of the following radicals in the 2-position: $C_1$-$C_6$-alkoximino, $C_3$-$C_6$-alkenyloximino, $C_3$-$C_6$-alkenyl or $C_3$-$C_6$-alkynyl, where these grous in turn may carry from one to five halogen atoms, or phenyl which is unsubstituted or monosubstituted to trisubstituted by $C_1$-$C_4$-alkyl or $C_1$-$C_4$-alkoxy or monosubstituted to pentasubstituted by halogen;

or $R^1$ is a radical ON=$CR^6R^7$, where $R^6$ and $R^7$ are each $C_1$-$C_{20}$-alkyl which may carry phenyl, $C_1$-$C_4$-alkoxy and/or $C_1$-$C_4$-alkylthio, or are each phenyl or together form a $C_3$-$C_{12}$-alkylene chain which may carry from one to three $C_1$-$C_3$-alkyl groups;

$R^2$ and $R^3$ are each $C_1$-$C_4$-alkyl, halogen, $C_1$-$C_4$-haloalkyl, $C_1$-$C_4$-alkoxy, $C_1$-$C_4$-haloalkoxy and/or $C_1$-$C_4$-alkylthio, n is zero, 1 or 2;

X is a nitrogen atom and Y is a methine group =CH—;

$R^4$ is hydrogen or $C_1$-$C_4$-alkyl;

A is an unsubstituted or monosubstituted to trisubstituted or, where halogen is the substituent, monosubstituted to pentasubstituted phenyl radical

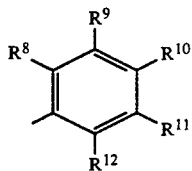

where $R^8$–$R^{12}$ are each hydrogen, halogen, cyano or nitro;
$C_3$–$C_6$-alkenyl, $C_3$–$C_6$-alkenyloxy, $C_3$–$C_6$-alkynyloxy or $C_3$–$C_6$-alkynyl, where these groups in turn may carry from one to five halogen atoms;
di-$C_1$–$C_4$-alkylamino, $C_3$–$C_8$-cycloalkyl which may carry from one to three $C_1$–$C_4$-alkyl radicals;
$C_1$–$C_{10}$-alkoxycarbonyl, $C_1$–$C_4$-alkylthio;
phenoxy, where the aromatic radical may carry from one to five halogen atoms and/or from one to three of the following radicals: $C_1$–$C_4$-alkyl, $C_1$–$C_4$-haloalkyl, $C_1$–$C_4$-haloalkoxy, $C_1$–$C_4$-alkoxy and $C_1$–$C_4$-alkylthio, or a $C_1$–$C_{10}$-alkyl or alkoxy group which may carry from one to five halogen atoms and/or one of the following radicals: $C_1$–$C_4$-alkoxy, $C_1$–$C_4$-alkylthio, phenyl or phenoxy, where the aromatic radicals in turn may carry from one to five halogen atoms and/or from one to three of the following radicals: $C_1$–$C_4$-alkyl, $C_1$–$C_4$-haloalkyl, $C_1$–$C_4$-haloalkoxy and $C_1$–$C_4$-alkylthio; or A is naphthyl which may carry from one to three halogen atoms and/or from one to three of the following radicals: $C_1$–$C_4$-alkyl or $C_1$- or $C_2$-haloalkyl, and environmentally compatible salts of the compound I.

2. A herbicidal composition comprising a carrier or diluent and a herbicidally effective amount of a compound of the formula I as defined in claim 1.

3. A method for controlling undesirable plant growth, wherein the undesirable plants and/or their habitat are treated with a herbicidally effective amount of a derivative I as defined in claim 1.

4. An agent for influencing plant growth, comprising a carrier or diluent in a growth regulating amount of a salicylic acid derivative of the formula I as defined in claim 1.

5. A method for regulating plant growth, wherein an amount, having a regulatory effect, of a salicylic acid derivative of the formula I as defined in claim 1 is allowed to act on the seeds, the plants and/or their habitat.